United States Patent [19] [11] 4,224,051
Clapot et al. [45] Sep. 23, 1980

[54] METHIONAL DERIVATIVES AND COMPOSITIONS WITH A GROWTH-REGULATING EFFECT UPON PLANTS

[75] Inventors: Claude Clapot, Oullins; Louis Dumont, Chaponost; Jean Vial, Tassin la Demi-Lune, all of France

[73] Assignee: Philagro, service Brevets, Lyons, France

[21] Appl. No.: 21,210

[22] Filed: Mar. 16, 1979

Related U.S. Application Data

[62] Division of Ser. No. 889,856, Mar. 24, 1978, Pat. No. 4,153,442, which is a division of Ser. No. 595,723, Jul. 14, 1975, Pat. No. 4,101,307.

[30] Foreign Application Priority Data

Jul. 15, 1974 [FR] France .................... 74 25781

[51] Int. Cl.³ .............................. A01N 59/02
[52] U.S. Cl. .............................. 71/98; 71/76; 71/78
[58] Field of Search ............... 260/609 R; 71/98, 76, 71/78

[56] References Cited
PUBLICATIONS

T. Yamanishi et al., Chem. Abst. 49:2300i (1955).
M. Huebner et al., Chem. Abst. 77:34561p (1972).

Primary Examiner—Donald G. Daus
Assistant Examiner—M. C. Eakin
Attorney, Agent, or Firm—Browdy and Neimark

[57] ABSTRACT

Plant growth-regulating compounds of the formula

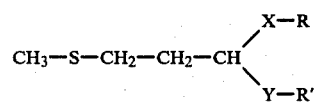

wherein X and Y are separately oxygen, sulfur, N-B where B is hydrogen, lower alkyl, or acyl; R and R' are separately lower alkyl, acyl, amido, or form a cycle with

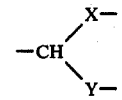

corresponding to the formula

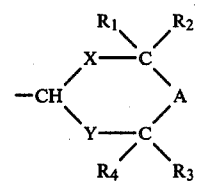

in which $R_1$, $R_2$, $R_3$, and $R_4$ are separately hydrogen, lower alkyl, halogen-substituted lower alkyl, $NO_2$, hydroxy or lower alkoxy, and A is a single bond or an alkylene chain of 1–4 carbons, or an alkylene chain of 1–4 carbons interrupted by oxygen or N-B' where B' is hydrogen, lower alkyl, lower halogen-aided alkyl, lower hydroxylated alkyl, lower acyl, or a cycle having in common with the preceding cycle 1 or 2 carbon atoms and containing from 3 to 6 carbons, up to 2 oxygens and/or a group N-B, or a cycle corresponding to the formula

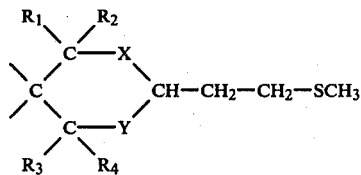

5 Claims, No Drawings

METHIONAL DERIVATIVES AND COMPOSITIONS WITH A GROWTH-REGULATING EFFECT UPON PLANTS

This is a division of copending application Ser. No. 889,856, filed Mar. 24, 1978, now U.S. Pat. No. 4,153,442, which is a division of application Ser. No. 593,723, filed July 14, 1975, now U.S. Pat. No. 4,101,307.

This invention relates to new methional derivatives and to compositions with a growth-regulating effect upon plants and containing methional derivatives.

In the context of the invention, the expression "growth regulator" is used in its accepted sense in the French language which corresponds to "growth substance" in the Anglo-Saxon literature, the term "growth" relating to the production of living material and not just to the modification of the size of plants. Accordingly, "growth regulators" in the context of the invention are products which are capable of modifying the physiology of plants in different ways.

The invention relates to methional compounds corresponding to the general formula

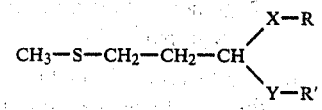

in which X and Y, which may be the same or different, represent oxygen, sulphur or a radical N—B where B is hydrogen, a lower alkyl radical containing 1 to 4 carbon atoms, an optionally substituted aryl radical or an optionally substituted acyl radical containing from 1 to 4 carbon atoms, R and R', which may be the same or different, represent a lower alkyl radical containing from 1 to 4 carbon atoms or an acyl or amido radical containing from 1 to 4 carbon atoms; in addition, they may form with

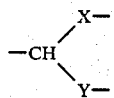

a cycle corresponding to the formula

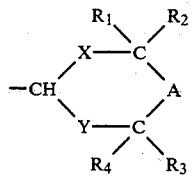

in which
$R_1$, $R_2$, $R_3$ and $R_4$, which may be the same or different, represent hydrogen, an alkyl radical containing from 1 to 4 carbon atoms and optionally substituted by a halogen, the radicals $NO_2$, hydroxy, alkoxy containing from 1 to 4 carbon atoms, A represents either a single bond or an alkylene chain containing from 1 to 4 carbon atoms optionally interrupted by an oxygen atom or a group N—B' where B' represents hydrogen, an optionally halogenated or hydroxylated alkyl group, an acyl group, the hydrocarbon portion of these radicals containing from 1 to 4 carbon atoms, or a cycle having in common with the preceding cycle 1 or 2 carbon atoms and containing from 3 to 6 carbon atoms, from 0 to 2 oxygen atoms and/or a group N—B, or a cycle corresponding to the formula

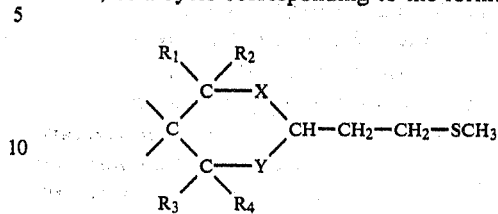

Some of these compounds, more especially the diethyl and ethylene acetals, have already been described in the literature, but never for their growth regulating properties.

The compounds according to the invention may be prepared, in cases where R and R' represent an alkyl, acyl or amido radical, by the action of β-methyl thiopropionaldehyde on a large excess of a compound containing in its functional group at least one mobile proton (alcohol, thiol, thiophenol, etc. . . ),

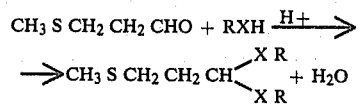

in cases where R and R' form a cycle, by the action of β-methyl thiopropionaldehyde on a compound containing in its chain two functional groups in the α- or β-position each containing at least one mobile proton

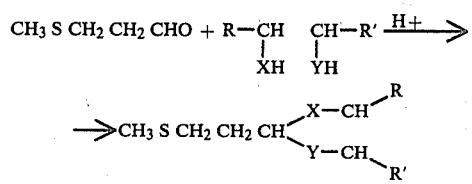

This condensation with dehydration is carried out in acid medium in the presence of an organic, more especially aromatic solvent, generally in admixture with a third solvent, such as dioxan or cellosolves. In cases where R and R' form a cycle, the reaction is carried out with entrainment of the water formed during the reaction. Products which are generally liquid at room temperature are obtained.

The following compounds were obtained by this method:
1,1-dimethoxy-3-methylthiopropane
1,1-diethoxy-3-methylthiopropane
1,1-di-n-propoxy-3-methylthiopropane
1,1-di-n-isopropoxy-3-methylthiopropane
1,1-di-n-butoxy-3-methylthiopropane
1,1-diacetyl-3-methylthiopropane
1,1-diacetamido-3-methylthiopropane
2-β-methylthioethyl-1,3-dioxolane
2-β-methylthioethyl-1,3-dithiolane
2-β-methylthioethyl-3-methyl-1,3-oxazolidine
2-β-methylthioethyl-5-methyl-1,3-dioxolane
2-β-methylthioethyl-5-chloromethyl-1,3-dioxolane
2-β-methylthioethyl-5-hydroxymethyl-1,3-dioxolane
2-β-methylthioethyl-5-methoxymethyl-1,3-dioxolane 2-β-methylthioethyl-4,5-dimethyl-1,3-dioxolane
2-β-methylthioethyl-4,4,5,5-tetramethyl-1,3-dioxolane
2-β-methylthioethyl-1,3-dioxane
2-β-methylthioethyl-4-methyl-1,3-dioxane
2-β-methylthioethyl-4,6-dimethyl-1,3-dioxane
2-β-methylthioethyl-5,5-dimethyl-1,3-dioxane
5,5'-β-spirobi-2-(β-methylthioethyl)-1,3-dioxane Another method of preparation comprises reacting with methional in an acid medium a (thio)ortho ester generally derived from formic acid and alcohols, optionally low molecular weight glycols, in accordance with the following scheme:

$$CH_3S-CH_2-CH_2-C\overset{H}{\underset{O}{\diagdown}}\overset{XR'}{\diagup} + HC\overset{YR'}{\underset{ZR'}{\diagdown}} \xrightarrow{H^+}$$

$$\longrightarrow CH_3S-CH_2-CH_2-C\overset{XR'}{\underset{YR'}{\diagdown}} + R'ZH$$

Z being an oxygen or sulphur atom. Suitable acid catalysts are ammonium chloride, anhydrous hydrochloric acid, concentrated sulphuric acid and p-toluene sulphonic acid.

Finally, it is possible to convert one acetal of methional into another richer in carbon by transacetalisation. This reaction may be used with particular advantage for the production of cyclic acetals from a linear acetal of methional and a diol (glycol, glycerol ...), for example in accordance with the following scheme:

$$CH_3S-CH_2-CH_2-CH\overset{OCH_3}{\underset{OCH_3}{\diagdown}} + \overset{HO}{\underset{HO}{\diagdown}}(CH_2)_{2\ or\ 3}$$

$$\longrightarrow CH_3S-CH_2-CH_2-CH\overset{O}{\underset{O}{\diagdown}}(CH_2)_{2\ or\ 3} + 2CH_3OH$$

Since the alcohol is the lightest, it is generally eliminated by distillation.

The preparation of the compounds according to the invention and their growth-regulating properties are illustrated by the following Examples.

EXAMPLE 1

Preparation of 1,1-dimethoxy-3-methylthiopropane (compound 1)

20.8 g (0.2 mole) of freshly distilled methional and 100 cc of methyl alcohol are heated under reflux in the presence of 0.5 g of p-toluene sulphonic acid.

A sample taken after 1 hour confirms that the reaction has taken place.

The methanol is then removed on a water bath and the residue rectified, giving a colourless liquid with a very strong fruity odour.

Yield: 58%, b.p.: 69° C./13 mm Hg, $n_D^{20}$: 1.4558.

Centesimal analysis for $C_6H_{14}O_2S$

| % | C | H |
|---|---|---|
| Calculated | 48.00 | 9.34 |
| Found | 48.31 | 9.45 |

EXAMPLE 2

Preparation of 1,1-diethoxy-3-methylthiopropane (compound 2)

The procedure is as in Example 1, except that the methanol is replaced by ethanol.

Yield: 66%, b.p.: 87°–90° C./17 mm Hg.

Centesimal analysis for $C_8H_{18}O_2S$

| % | C | H | S |
|---|---|---|---|
| Calculated | 53.93 | 10.11 | 17.97 |
| Found | 53.94 | 10.14 | 17.97 |

EXAMPLE 3

Preparation of 2-(β-methylthioethyl)-1,3-dioxolane (compound 3)

1040 g (10 moles) of freshly distilled methional, 650 g (10.5 moles) of ethylene glycol, 400 cc of benzene, 800 cc of dioxan and 10 g of p-toluene sulphonic acid are heated under reflux until the azeotropic entrainment of the water formed during the reaction, which takes 2 hours, is over. The acid medium is then neutralised by the addition of 10 g of dry sodium carbonate, after which the solution is concentrated to dryness in a water pump vacuum.

The residual oil is re-solubilised in 1 liter of toluene to enable the solution to be washed with water, a second time with a solution of sodium bisulphite and finally a third time with water. The toluene is then evaporated and the residue distilled, giving a colourless liquid with a very strong fruity odour.

Yield: 82%, b.p.: 89° C./12 mm Hg, $n_D^{20}$: 1.4830.

Centesimal analysis for $C_6H_{12}O_2S$

| % | C | H | S |
|---|---|---|---|
| Calculated | 48.65 | 8.11 | 21.62 |
| Found | 48.33 | 8.07 | 21.63 |

EXAMPLES 4 TO 17

Compounds 4 to 17 are prepared by the same method as before. The following Tables show the yields and characteristics of the products obtained.

In the developed formulae of the products, the radical $CH_3SCH_2-CH_2-CH<$ is shown in abbreviated form as Met<

| Compound No. | FORMULA | STRUCTURE OBTAINED Empirical formula | Physical characteristics | Yield | | CENTESIMAL ANALYSIS | | | |
|---|---|---|---|---|---|---|---|---|---|
| 4 | Met(S—CH₂—S—CH₂) | $C_6H_{12}S_3$ | b.p. 103° C./0.15 mm Hg $n_D^{20} = 1.5920$ | 83% | C<br>F | C%<br>40.0<br>40.10 | H%<br>6.67<br>6.76 | | S%<br>53.33<br>53.26 |
| 5 | Met(N(CH₃)—CH₂—O—CH₂) | $C_7H_{15}NOS$ | b.p. 50°–55° C./0.06 mm Hg $n_D^{20} = 1.4930$ | 52.5% | C<br>F | C%<br>52.17<br>52.13 | H%<br>9.32<br>9.38 | N%<br>8.63<br>8.69 | S%<br>19.87<br>19.87 |
| 6 | Met(O—CH₂—O—CHCH₃) | $C_7H_{14}O_2S$ | b.p. 99° C./15 mm Hg $n_D^{20} = 1.4730$ | 71.3% | C<br>F | C%<br>51.85<br>51.86 | H%<br>8.64<br>8.78 | | S%<br>19.75<br>19.78 |
| 7 | Met(O—CH₂—O—CH—CH₂Cl) | $C_7H_{13}ClO_2S$ | b.p. 80–81/0.04 mm Hg $n_D^{20} = 1.4380$ | 71.5% | C<br>F | C%<br>42.74<br>42.67 | H%<br>6.61<br>6.61 | Cl%<br>18.06<br>18.16 | S%<br>16.26<br>16.19 |
| 8 | Met(O—CH₂—O—CH—CH₂OH) | $C_7H_{14}O_3S$ | b.p. 96° C./0.02 mm Hg $n_D^{20} = 1.5000$ | 60.6% | C<br>F | C%<br>47.19<br>46.97 | H%<br>7.86<br>7.84 | | S%<br>17.97<br>17.96 |
| 9 | Met(O—CH₂—O—CH—CH₂OCH₃) | $C_8H_{16}O_3S$ | b.p. 70°–90° C./0.03 mm Hg $n_D^{20} = 1.4760$ | 88.5% | C<br>F | C%<br>50.00<br>50.05 | H%<br>8.33<br>8.44 | | S%<br>16.66<br>16.61 |
| 10 | Met(O—CH—CH₃, O—CH—CH₃) | $C_8H_{16}O_2S$ | b.p. 70° C./0.04 mm Hg $n_D^{20} = 1.4685$ | 83.8% | C<br>F | C%<br>54.55<br>54.63 | H%<br>9.09<br>9.12 | | S%<br>18.18<br>18.16 |
| 11 | Met(O—C(CH₃)₂—O—C(CH₃)₂) | $C_{10}H_{20}O_2S$ | b.p. 80°–81° C./0.04 mm Hg $n_D^{20} = 1.4695$ | 35.8% | C<br>F | C%<br>58.82<br>58.94 | H%<br>9.80<br>9.88 | | S%<br>15.69<br>15.64 |
| 12 | Met(O—CH₂—CH₂—O—CH₂) | $C_7H_{14}O_2S$ | b.p. 70° C./0.025 mm Hg $n_D^{20} = 1.4860$ | 81.5% | C<br>F | C%<br>51.85<br>51.86 | H%<br>8.64<br>8.58 | | S%<br>19.75<br>19.68 |
| 13 | Met(O—CH(CH₃)—CH₂—O—CH₂) | $C_8H_{16}O_2S$ | b.p. 68° C./0.015 mm Hg $n_D^{20} = 1.4780$ | 80.9% | C<br>F | C%<br>54.55<br>54.56 | H%<br>9.09<br>9.03 | | S%<br>18.18<br>18.25 |
| 14 | Met(O—CH(CH₃)—CH₂—O—CH(CH₃)) | $C_9H_{18}O_2S$ | b.p. 74° C./0.03 mm Hg $n_D^{20} = 1.4735$ | 75.6% | C<br>F | C%<br>56.84<br>56.88 | H%<br>9.47<br>9.54 | | S%<br>16.84<br>16.96 |
| 15 | Met(O—CH₂—C(CH₃)₂—O—CH₂) | $C_9H_{18}O_2S$ | b.p. 10.8/0.04 mm Hg $n_D^{20} = 1.4748$ | 89.2% | C<br>F | C%<br>56.84<br>56.90 | H%<br>9.47<br>9.54 | | S%<br>16.84<br>16.76 |
| 16 | Met(O—CH₂—C(NO₂)(CH₃)—O—CH₂) | $C_8H_{15}NO_4S$ | m.p. 61° C. | 70% | C<br>F | C%<br>43.43<br>43.40 | H%<br>6.79<br>6.69 | N%<br>6.33<br>6.11 | S%<br>14.48<br>14.61 |

| Compound No. | FORMULA | STRUCTURE OBTAINED Empirical formula | Physical characteristics | Yield | CENTESIMAL ANALYSIS | | |
|---|---|---|---|---|---|---|---|
| | | | | | C% | H% | S% |
| 17 | Met−O−CH₂\C/CH₂O−Met / O−CH₂ CH₂O | $C_{13}H_{24}O_4S_2$ | b.p. 165°–170° C./ 0.04 mm Hg | 74.7% | C 50.65 F 50.57 | 7.79 7.98 | 20.78 20.71 |

EXAMPLE 18

Preparation of 1,1-di-n-propoxy methyl thiopropane (compound 18)

The procedure is as in Example 1, except that the methanol is replaced by n-propanol.
Yield: 90%.
Centesimal analysis for $C_{10}H_{22}O_2S$:

| % | C | H | S |
|---|---|---|---|
| Calculated | 58.25 | 10.68 | 15.23 |
| Found | 58.21 | 10.65 | 15.49 |

EXAMPLE 19

Preparation of 1,1-di-n-butoxy methylthiopropane (compound 19)

The procedure is as in Example 1 except that the methanol is replaced by n-butanol.
Yield: 84%
Centesimal analysis for $C_{12}H_{26}O_2S$:

| % | C | H | S |
|---|---|---|---|
| Calculated | 61.54 | 11.11 | 13.67 |
| Found | 61.63 | 11.18 | 13.66 |

The biological properties of the compounds according to the invention are demonstrated by tests in which the plants or seeds are treated by several methods which are essentially governed by the type of plants used for the tests and by the expected responses.

The term "solution" used hereinafter means either an aqueous solution if the active material is soluble in water or, in the opposite case, an aqueous dispersion of a 20% wettable powder of the active material or an emulsifiable concentrate containing 100 g/l of active material.

In a first method of treatment, so-called root treatment, applicable to peas, 2 to 6 day old plants of two varieties, one dwarf "Petit Provencal" and the other giant "Alaska", are placed on the surface of a solution containing from 1 to 10 g/l of the material to be tested, the root being submerged. After 3 to 5 days, the biometric and morphological development of the plants is observed and noted.

In the case of other plants, such as beans, tomatoes, maize, cotton, turnsole, gherkin, chrysanthemum, at the 2 to 4 leaf stage, and in the case of fruit trees, pineapples, etc., the leaves are treated by spraying with a solution containing from 1 to 10 g/l of the material to be tested. The biometric and morphological development of the plants is measured after 8 days, 25 days, 1 month and even 6 months in the case of certain plants such as fruit trees.

In the case of such plants as maize, tomatoes, tobacco, cotton, barley, peas, mustard, it is also possible to immerse seeds thereof for 24 hours in a solution containing from 0.01 to 10 g/l of the material to be tested. The seeds thus treated are then sown. Their biometric and morphological development as a function of time is noted.

For most of the tests on barley, the seeds of this plant are geminated on the surface of a solution containing from 0.01 to 10 g/l of the material to be tested. The biometric and morphological development of the plants is noted after 3 and 5 days.

Finally, in certain tests relating to the ripening of fruit, measured green fruits taken from the same level of the plant are immersed for 24 hours in a solution containing from 1 to 10 g/l of the material to be tested. The advance of external and internal ripening of the fruit is noted.

Several modes of action of the products according to the invention on the growth of the above-mentioned plants are studied by these methods in the following Examples.

EXAMPLE I

Reduction in size

The size of the epicotyls and the distances between nodes of the plants treated are measured in relation to controls.

Under these conditions, a reduction in size of from 16 to 45% is obtained with doses of from 0.1 to 5 g/l of compounds 1 to 19 in beans, compound 2 in maize and compounds 3 and 4 in tomatoes.

EXAMPLE II

Modification of the development of side shoots

The number of side shoots are counted and their length measured as a function of time.

Under these conditions, it is found that, in doses of from 0.1 to 10 g/l, compound 2 brings about an increase in branching and a significant development of side shoots in tomatoes, beans and chrysanthemums, whilst compounds 3 and 4 retard the development of side shoots.

EXAMPLE III

Effect on the ripening and colouring of fruit

Green tomatoes (*Lycopersicum aesculentum*) of the Marmande variety are steeped in the products to be tested, one control being reserved for comparison. After steeping, the tomatoes are placed in open transparent containers under glass.

Under these conditions, it is found that, whereas the controls ripen in 12 days, the fruit treated with compounds 1 to 17 ripens in 4 days.

EXAMPLE IV

Action on flowering and fructification

The number of flowers and/or fruits of the treated plants are noted in relation to an untreated control. The delays or advances in flowering are also observed.

Under these conditions, it is found that, in a dose ranging from 0.01 to 0.1 g/l, compounds 12 to 15 reduce by 40% the number of small bean plants, thereby thinning them out, the remaining fruits being larger, which results in a 60% increase in the number of beans picked, and advance the flowering of bean plants by 4 to 5 days.

EXAMPLE V

Epinasty effect

The deformation caused by twisting in the stems of the plants is observed. Under these conditions, it is found that, in a dose of 10 g/l, compounds 1 to 17 cause heavy deformation in peas treated by the root method.

These Examples clearly illustrate the remarkable properties of the compounds according to the invention which may thus be used for plants of all kinds, such as plants grown on a large scale and on a commercial scale, cereals, fruits, vegetables, ornamental plants, medicinal plants and perfume plants, with a view to increasing the yields, facilitating collection, for example by abscission of the leaves, accelerating ripening of fruit, promoting branching, modifying habit, producing floral induction (flowering), delaying blossoming as a preventive measure against frosts, reducing size in order to obtain more compact plants, etc.

The doses which may be used vary within wide limits in dependence upon the required effect, the type of plant, its stage of treatment, the soil and climatic conditions. Generally, doses ranging from 0.01 to 10 g/l are entirely adequate.

For their practical application, the compounds according to the invention are rarely used on their own. In most cases, they form part of formulations which generally contain a support and/or a surfactant in addition to the active material according to the invention.

In the context of the invention, a "support" is any organic or mineral, natural or synthetic material with which the active material is associated to facilitate its application to the plant, to seeds or to the soil, or its transportation or handling. The support may be solid (clays, natural or synthetic silicates, resins, waxes, solid fertilisers . . . ) or fluid (water, alcohols, ketones, petroleum fractions, chbrinated hydrocarbons, liquefied gases). The surfactant may be an ionic or non-ionic emulsifier, dispersant or wetting agent. Examples of suitable surfactants are salts of polyacrylic acids, lignin sulphonic acids, condensates of ethylene oxide with fatty alcohols, fatty acids or fatty amines.

The compositions according to the invention may be prepared in the form of wettable powders, dusting powders, granulates, solutions, emulsifiable concentrates, emulsions, suspended concentrates and aerosols.

The wettable powders according to the invention may be prepared in such a way that they contain from 20 to 95% by weight of active material, and they normally contain, in addition to a solid support, from 0 to 5% of a wetting agent, from 3 to 10% by weight of a dispersant and, where necessary, from 0 to 10% by weight of one or more stabilisers and/or other adhesives as penetration agents, adhesives or antilumping agents, colorants, etc.

One example of the composition of a wettable powder is given below, the percentages being expressed as percent by weight:
active material: 50%
calcium lignosulphate (deflocculant): 5%
isopropyl naphthalene sulphonate (wetting agent): 1%
antilumping silica: 5%
kaolin filler: 39%

The emulsifiable concentrates which may be applied by spraying normally contain in addition to the solvent and, where necessary, a co-solvent, from 10 to 50% by weight/volume of active material, from 2 to 20% by weight/volume of suitable additives such as stabilisers, penetration agents, corrosion inhibitors, and colorants and adhesives.

One example of the composition of an emulsifiable concentrate is given below, the quantities being expressed in g/liter:
active material: 400 g/l
dodecylbenzene sulphonate: 24 g/l
nonylphenol ethoxylated to 10 molecules: 16 g/l
cyclohexanone: 200 g/l
aromatic solvent: q.s.f. 1 liter The suspended concentrates, which may also be applied by spraying, are prepared in such a way that the end product is a stable non-sedimenting fluid. They normally contain from 10 to 75% by weight of active material, from 0.5 to 15% by weight of surfactants, from 0.1 to 10% by weight of anti-sedimenting agents, such as protective colloids and thixotropic agents, from 0 to 10% by weight of suitable additives, such as antifoaming agents, corrosion inhibitors, stabilisers, penetration agents and adhesives, and as support water or an organic liquid in which the active material is substantially insoluble. Certain organic solid materials or mineral salts may be dissolved in the support in order to assist in preventing sedimentation or as antifreeze agents for the water.

Aqueous dispersions and emulsions, for example compositions obtained by diluting with water a wettable powder or an emulsifiable concentrate according to the invention, fall within the general scope of the invention. These emulsions may be of the water-in-oil type or of the oil-in-water type and may have a thick consistency resembling that of a "mayonnaise".

The compositions according to the invention may contain other ingredients, for example protective colloids, adhesives or thickeners, thixotropic agents, stabilisers or sequestrants, and other active materials known to have pesticidal properties, more especially insecticides, fungicides or growth regulators.

All these compositions may be applied to the plants by various methods such as spraying onto the aerial part of the plants, steeping seeds, plants, balls, roots or fruits, sprinkling of soil, injection into the plant, etc.

We claim:

1. A process for modifying the growth of a plant comprising applying to said plant a growth-modifying amount of a compound of the formula

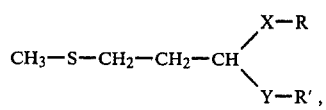

wherein

X and Y, which may be the same or different, are each O, or S; and

R and R', which may be the same or different, are each lower alkyl of 1-4 carbons.

2. A process in accordance with claim 1 wherein X and Y are both sulfur; or X is sulfur and Y is oxygen.

3. A process in accordance with claim 1, wherein said compound is selected from the group consisting of 1,1-dimethoxy-3-methylthiopropane; 1,1-diethoxy-3-methylthiopropane; 1,1-di-n-propoxy methylthiopropane; and 1,1-di-n-butoxy methylthiopropane.

4. A growth-regulating composition for plants, comprising (a) an agricultural carrier, (b) a surfactant and (c) an amount sufficient to regulate the growth of plants of a compound of the formula

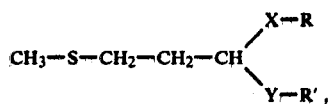

wherein
X and Y, which may be the same or different, are each O, or S; and
R and R', which may be the same or different, are each lower alkyl of 1-4 carbons.

5. A composition in accordance with claim 4 wherein X and Y are both sulfur; or X is sulfur and Y is oxygen.

* * * * *